(12) United States Patent
Yamada

(10) Patent No.: US 6,474,344 B2
(45) Date of Patent: Nov. 5, 2002

(54) ARTIFICIAL HAIR FOR IMPLANTATION AND PROCESS FOR PRODUCING THE ARTIFICIAL HAIR

(76) Inventor: Shiro Yamada, 7-1-606, Mita 2-chome, Minato-ku, Tokyo 108-0073 (JP)

( * ) Notice: Subject to any disclaimer, the term of this patent is extended or adjusted under 35 U.S.C. 154(b) by 0 days.

(21) Appl. No.: 09/775,541

(22) Filed: Feb. 5, 2001

(65) Prior Publication Data

US 2001/0011544 A1 Aug. 9, 2001

(30) Foreign Application Priority Data

Feb. 3, 2000 (JP) .......................................... 2000-23602
Jan. 12, 2001 (JP) .......................................... 2001-4808

(51) Int. Cl.⁷ ................................................. A61F 2/10
(52) U.S. Cl. ..................................... 132/201; 623/15.11
(58) Field of Search ................ 132/201, 53; 623/15.11; 28/219

(56) References Cited

U.S. PATENT DOCUMENTS

| | | | | |
|---|---|---|---|---|
| 3,786,822 A | * | 1/1974 | Kimura et al. | ................ 132/53 |
| 4,729,913 A | * | 3/1988 | Matsui et al. | ................ 132/53 |
| 4,773,135 A | * | 9/1988 | Sato et al. | |
| 4,793,368 A | | 12/1988 | Yamada | |
| 4,839,132 A | * | 6/1989 | Wang | |
| 4,880,428 A | | 11/1989 | Yamada | |
| 5,005,596 A | | 4/1991 | Yamada | |
| 5,595,750 A | * | 1/1997 | Jacobson et al. | |
| 6,296,934 B1 | * | 10/2001 | Needham et al. | |

* cited by examiner

Primary Examiner—Todd E. Manahan
(74) Attorney, Agent, or Firm—Browdy and Neimark, P.L.L.C.

(57) ABSTRACT

A monofilament fabricated by a process in which a melt spinning and drawing treatment are carried out after particles of silver ceramics are mixed with a resin material for a fiber having a principal component of polybutylene terephthalate. The particles of the silver ceramics have a size of 5.0 $\mu$m or less, and the content of the particles of the silver ceramics in the mixture is within a range of 0.3% to 3.0%. The monofilament thus obtained is suitably cut and a root part is formed at one end of the monofilament. Then, the surface of the monofilament is subjected to a mechanical delustering treatment, thus obtaining artificial hair having low bacterial infection rate, high fixation rate of implanted hairs, and high durability, such that the hair does not break at a point near the root part even after having been used for a long period of time after implantation.

18 Claims, 3 Drawing Sheets

Comparing Test for Rigidities of Various Kinds of Artificial Hairs

| Samples | Vertical Displacement δ |
|---|---|
| Artificial Hair made of Polybutylene Terephthalate (PBT) without Silver Ceramics | 8.50 mm |
| Artificial Hair made of Polybutylene Terephthalate (PBT) with 1.5% Silver Ceramics | 6.44 mm |
| Artificial Hair made of Polyetylene Terephthalate (PET) | 3.12 mm |

Fig. 1

Number of Viable Fungi on the Sample inoculated the test Fungus

Test Fungus: Staphylococus Aureus

| Samples | | Number of Viable Fungi | |
|---|---|---|---|
| | | Immediately after the Inoculation | 18 hours after the Inoculation |
| Sample A | Hair #1<br>Hair #2 | $1.3 \times 10^4$<br>$1.6 \times 10^4$ | $1.3 \times 10^3$<br>$1.8 \times 10^2$ |
| Sample B | Hair #1<br>Hair #2 | $1.3 \times 10^4$<br>$1.6 \times 10^4$ | Not detected<br>Not detected |
| Sample C | Hair #1<br>Hair #2 | $1.3 \times 10^4$<br>$1.6 \times 10^4$ | $1.0 \times 10^7$<br>$1.8 \times 10^6$ |

Note: The number of viable fungi is a number per a hair of each sample.

Fig. 4

ARTIFICIAL HAIR FOR IMPLANTATION AND PROCESS FOR PRODUCING THE ARTIFICIAL HAIR

FIELD OF THE INVENTION

The present invention relates to artificial hair for implantation which is suitable for direct implantation into the skin of a living human body, and a process for producing the artificial hair.

BACKGROUND

Many kinds of artificial hair for implantation directly into skin of a human body have been proposed. Among these kinds of artificial hair, those which have found practical acceptance include artificial hair with a loop-shaped root part, which is developed by the present inventor and is disclosed in Japanese Patent Publication No. H03-8770 and U.S. Pat. No. 4,793,368. On the basis of the invention disclosed in the above-mentioned patent documents, a monofilament of polyethylene terephthalate (PET) fiber is most desirably employed in this type of artificial hair.

Polyethylene terephthalate fiber has proven to be very safe for human implantation since it is subjected to melt spinning without using an organic solvent, and it also has excellent strength and durability. As a consequence, polyethylene terephthalate has been believed to be the most suitable material for artificial hair.

However, it has been found that, when artificial hair made of polyethylene terephthalate fiber is actually implanted and used for long periods of time, many strands break at points in the vicinity of the roots and fall off. Therefore, in order to solve this problem, the present inventor carried out a test of repeated 180 degree bending at the same place of a single polyethylene terephthalate fiber (i.e., bending fatigue test), and determined that a monofilament having a diameter of 91 μm breaks after it has been bent in this manner about 50,000 times.

In addition, there is another problem that the artificial hair strands fall off due to suppuration at root parts of the artificial hair caused by infection with bacteria during their implantation, thus causing deterioration in the fixation rate of the implanted artificial hair. As a countermeasure to this problem, a method of attaching amorphous silver in spots to the surface of the artificial hair so as to prevent infection due to bacteria during the implantation operation and prevent suppuration due to the bacteria after implantation has been proposed, as disclosed in Japanese Patent Publication No. H04-48460 and U.S. Pat. No. 5,005,596.

However, the method of attaching amorphous silver in spots to the surface of the artificial hair needs complicated and expensive apparatus and, in addition, there is a problem that the vacuum deposition conditions are difficult to control for achieving uniform adherence of the amorphous silver to the surface of the artificial hair.

SUMMARY OF THE INVENTION

In order to solve the above-mentioned problems, the present invention provides artificial hair for implantation, which has a high fixation rate of implanted artificial hair strands and high durability such that the artificial hair strands do not break at a root part even after having been used for long periods of time after implantation.

The present invention further provides artificial hair for implantation, which has a low bacterial infection rate, a high fixation rate of implanted artificial hair and high durability such that the artificial hair does not break at a root part even after having been used for long periods of time after implantation.

Further, the present invention provides a process for producing, at a low cost and with simple operations, artificial hair for implantation, which has a high fixation rate of implanted artificial hairs and high durability such that the artificial hair does not break at a root part even after having been used for long periods of time after implantation.

Furthermore, the present invention provides a process for producing, at a low cost and with simple operations, artificial hair for implantation, which has a low bacterial infection rate, a high fixation rate of implanted artificial hairs, and high durability such that the artificial hair does not break at a root part even after having been used for long periods of time after implantation.

As the result of intensive research carried out by the present inventor in order to achieve the above-mentioned objects, artificial hair using a fiber comprising polybutylene terephthalate as its principal component has proven to successfully attain the foregoing objects.

Specifically, an artificial hair strand according to the present invention is characterized in that it is made of a monofilament of a fiber comprising as a principal component polybutylene terephthalate (PBT). Polybutylene terephthalate is known and has been used to make paint brush bristles. It is obtained from direct polycondensation between a terephthalic acid and 1,4-butanediol; or from polycondensation by transesterification between dimethyl terephthalate and 1,4-butanediol. Polyethylene terephthalate is often used for films and fibers, whereas polybutylene terephthalate has been principally used to make molded products. The PBT used inn the practice of the present invention is preferably a compound having a number average molecular weight of 10,000 to 60,000, and preferably 20,000 to 40,000.

Polybutylene terephthalate fiber is usually fabricated by subjecting a polybutylene terephthalate masterbath to melt spinning. In order to produce the artificial hair, the fiber is subjected to a drawing treatment so as to obtain monofilaments having a diameter within a range of 80 μm to 110 μm, and preferably 90 μm to 100 μm. Depending on various applications, pigments may be added to the raw material before the spinning so as to color the artificial hair suitably into black, brown, gray or other colors. The pigments used in the artificial hair are preferably present in an amount less than 3% by weight and are typically carbon black, iron oxide, titanium oxide, or the like. The pigments can be used singly or in the form of a mixture. A root part is formed at one end of the obtained monofilament, for example as disclosed in the first patent documents cited above, and thus the artificial hair is produced.

Artificial hair made of monofilaments of polybutylene terephthalate has substantially the same tensile strength, chemical resistance, light resistance and other properties as those of artificial hair made of monofilaments of polyethylene terephthalate. On the other hand, artificial hair made of monofilaments of polybutylene terephthalate has extremely greater bending fatigue-resistant strength (i.e., the durability in a bending fatigue test) than artificial hair made of monofilaments of polyethylene terephthalate.

Specifically, results of a bending test in which monofilaments are bent repeatedly through 180 degrees at the same place until the monofilament is broken reveal that polyethylene terephthalate fiber breaks after having been bent about 50,000 times, while polybutylene terephthalate fiber does not break even when the number of times of bending reaches 1,500,000. This physical property of polybutylene terephthalate fiber is extremely effective in improving the durability of the artificial hair after implantation.

However, compared to polyethylene terephthalate fiber, polybutylene terephthalate fiber has extremely low lateral stiffness. As a consequence, artificial hair made of polybutylene terephthalate fiber would normally be too soft and therefore would stick to the scalp in an undesired manner.

In order to improve the stiffness of polybutylene terephthalate fiber, the present inventor has ascertained that incorporation into the fiber of a powder of silver ceramics can attain the best results in increasing lateral stiffness without significant diminution of other properties.

Specifically, artificial hair for implantation according to the present invention is characterized by being made of a monofilament of a fiber comprising a principal component of polybutylene terephthalate containing powder of silver ceramics. The silver ceramics used in the present invention include, for example, silver zeolite, silver apatite, silver phosphoric acid calcium, silver phosphoric acid zirconium, and so on. Generally, such silver ceramics may be produced by an ion-exchange reaction between a ceramic and silver ions.

BRIEF DESCRIPTION OF THE DRAWINGS

FIG. 1 is a table showing the results of tests comparing rigidities of various kinds of artificial hair.

FIG. 4 is a table showing results of tests for comparing the antibacterial abilities of various kinds of artificial hairs.

DETAILED DESCRIPTION OF THE INVENTION

Figure 2:
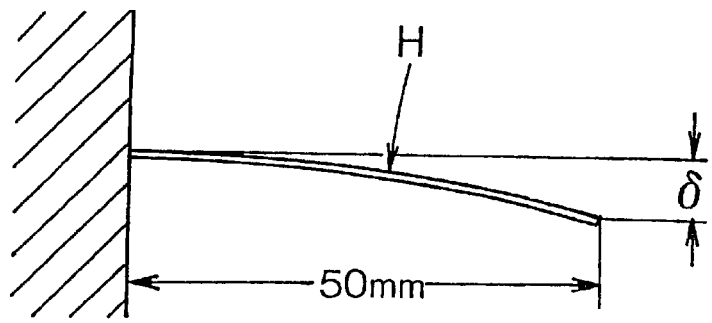
FIG. 2 is a drawing showing a test arrangement for measuring the stiffness of artificial hair.

Preferred embodiments of monofilaments according to the invention contain a powder of silver ceramics to be used as an additive to the artificial hair, the powder having a maximum particle, or grain, size of 5.0 $\mu$m or less and an average particle, or grain, size of 2–3 $\mu$m.

The artificial hair monofilaments have, in general, a diameter within a preferred range of 90 $\mu$m to 100 $\mu$m. Therefore, the use of powder additive with particles larger than 5.0 $\mu$m is not preferable since it would deteriorate the tensile strength as well as the bending strength of the artificial hair and also result in a product with a grayish color tone depending on the particular type of the powder additive.

While the particle size of the silver ceramics powder is preferably as small as possible, it is actually difficult to obtain the powder having a particle size of 1 $\mu$m or less. Therefore, powder having a particle size of about 2 $\mu$m is actually used.

The content of the powder of the silver ceramics in the mixture is preferably within the range of 0.3% to 3.0% by weight, and particularly preferably about 1.5% by weight with respect to the amount of the fibrous material comprising the principal component of polybutylene terephthalate. If the content of the powder of the silver ceramics is smaller than 0.3%, the effect of improving the stiffness is hardly attained. However if the content of the power of the silver ceramics is higher than 3.0%, the stiffness increases to an excessive level, thus resulting in artificial hair having insufficient flexibility. Consequently, a content of the silver ceramics powder either lower or higher than the abovementioned range is not preferable.

The silver ceramics used in artificial hair according to the invention are preferably silver zeolite, silver apatite, silver phosphoric acid calcium, silver phosphoric acid zirconium, or the like. Silver zeolite can be produced by adding a silver nitrate aqueous solution to fine zeolite powder, and agitating the resulting mixture. The silver zeolite is obtained by an ion exchange reaction between the zeolite and the silver ions of the silver nitrate. A suitable form of silver zeolite is marketed by the company Kanebo Kasei KK under the trademark BACTEKILLER.

The addition of the powder of the silver ceramics can, as disclosed above, achieve the effect of improving the stiffness of the artificial hair comprising polybutylene terephthalate as its principal component, and can simultaneously improve the antibacterial effect of the artificial hair owing to the silver contained in the silver ceramic. When the artificial hair is implanted into the scalp, bacteria may invade though incisions formed in the skin incident to the implantation operation and thus cause suppuration.

However, if the silver ceramics are blended into the artificial hair, suppuration can be prevented due to the bactericidal effect of the silver ceramics, and the fixation rate of the implanted artificial hairs can be improved. Other suitable additives include pigments. Preferably, the pigment content will be between 0.1 and 3%, by weight, the silver ceramics content will be between 0.3 and 3%, by weight, and the total additive content will be not greater than 6%, by weight.

The artificial hair made of the polybutylene terephthalate fiber is preferably subjected to a surface delustering treatment since the polybutylene terephthalate fiber has an inherent glossy appearance. The surface delustering treatment is preferably carried out by using, for example, a mechanical delustering method developed by the present inventor and disclosed in Japanese Patent Publication No. H02-1765 and U.S. Pat. No. 4,880,428.

Specifically, as disclosed in the abovementioned patent publications, the surface delustering treatment is carried out by holding a bundle of monofilaments of the artificial hair between two abrading sheets which have soft layers on their surface, and then, in the presence of an abrasive material, reciprocating the two abrading sheets in relatively opposite directions while applying a low pressure onto the abrading sheets, whereby innumerable irregular abrasions are formed in the surfaces of the monofilaments so as to provide the surfaces of the artificial hair with gloss similar to the surface gloss of real human hair.

Particularly, the mechanical surface delustering treatment of the artificial hair with the powder of silver ceramic blended therein has another advantage that the bactericidal effect can be further improved since the surfaces of the blended silver ceramic particles in the vicinity of the surface of the artificial hair are scraped to be exposed at the surface of the artificial hair strands, or monofilaments.

The following examples are offered illustratively.

EXAMPLES

Monofilaments were fabricated by melt-spinning a blend comprising the following components:
polybutylene terephthalate
   (number average molecular weight 32,000) 100 parts
silver zeolite
   (particle size: 2 $\mu$m; BACTEKILLER®) 1.5 parts pigment:
    (carbon black) 0.7 parts
    (iron oxide) 0.1 parts Then, the monofilaments were subjected to a drawing treatment so as to obtain raw monofilament threads for artificial hair strand having a diameter of 90 μm.

A bundle of the raw threads for the artificial hair were held between two abrading sheets having sponge layers on their surfaces. Then, in the presence of an abrasive material, the two abrading sheets were reciprocated in opposite directions to one another while having a low pressure applied onto the abrading sheets, whereby innumerable abrasions were formed in the surfaces of the monofilaments, thus accomplishing the delustering treatment.

An end of each monofilament having been subjected to the delustering treatment was melted and shaped into a loop to form a root part, for example in a manner disclosed in the previously cited patent documents, and thus the artificial hair was completed.

Physical properties of this artificial hair formed as described above are shown as follows:

tensile strength (cN)—314;
    elongation rate(%)—40.6;
    knot strength (cN)—258;
    loop strength (cN)—509;
    melting point (OC)—224.1;
    appearance fineness (D,) 80.1; and
    bending fatigue/breaking strength—the artificial hair did not break even when after having been bent 1,500,000 times.

The artificial hair also has excellent chemical resistance and color fastness.

Stiffness of Artificial Hair

FIG. 1 shows the results of tests comparing the stiffness of various kinds of artificial hair. Specifically, five strands, or monofilaments, each of artificial hair made of polybutylene terephthalate (PBT) without addition of silver zeolite, artificial hair made of polybutylene terephthalate (PBT) with addition of 1.5% silver zeolite, and artificial hair made of polyethylene terephthalate (PET) were used as samples to carry out the tests according to a test method which will be described below. Average values of the test results are shown in FIG. 1.

The tests are carried out, as shown in FIG. 2, by fixing a base portion of an artificial hair monofilament H to a support to horizontally hold a portion extending 50 mm from the base portion. At this time, the vertical distance δ between the tip and the base portion of the monofilament was measured to determine its stiffness.

As shown in FIG. 1, the displacement of artificial hair made of polyethylene terephthalate (PET) is 3.12 mm, which is the smallest among the displacement amounts of the three samples. This result reveals that the artificial hair made of polyethylene terephthalate (PET) has the highest stiffness. Practical experience with artificial hair made of this material shows that it is too hard and tends to stand up.

The displacement amount of artificial hair made of polybutylene terephthalate (PBT) without addition of silver zeolite is 8.50 mm which is the greatest among the displacement amounts of the three samples. This result reveals that artificial hair made of PBT without addition of silver zeolite is too soft and easy to break. Actual implants of artificial hair made of PBT without the addition of silver zeolite tend to stick on the scalp and it is therefore difficult to create a fluffy hairstyle with this material.

The displacement amount of artificial hair made of polybutylene terephthalate (PBT) with addition of 1.5% silver zeolite is 6.44 mm, which reveals that this artificial hair has a stiffness greater than that of the artificial hair made of PBT without addition of silver zeolite, and can attain a feel approximating that of natural human hair. The preferred range of vertical displacement to obtain the most desirable mechanical properties is between 5 and 7 mm.

Tensile Stress Characteristics of Artificial Hair

Figure 3:
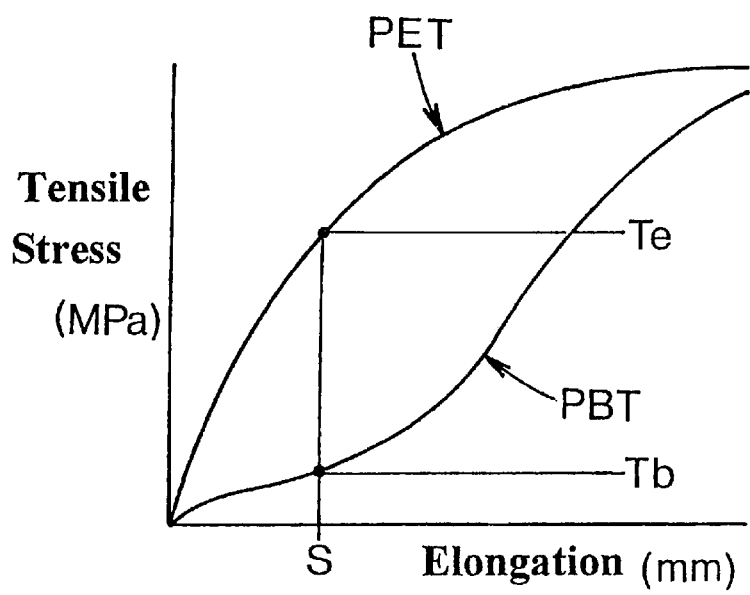
FIG. 3 is a graph showing a correlation between tensile stress and elongation of artificial hair.

This property can be explained by reference to the graph of FIG. 3, which show the correlation between elongation and tensile stress of the artificial hair. The curve labeled PET relates to polyethylene terephthalate artificial hair monofilaments and shows a higher tensile stress Te with respect to a certain elongation S. This indicates that artificial hair made of PET tends to deform due to bending or folding. On the other hand, the curve labeled PBT relates to polybutylene terephthalate artificial hair monofilaments and shows a lower tensile stress Tb for the same elongation S, and this reveals that artificial hair made of PBT is flexible and therefore does not easily deform due to bending.

Actually, experience with implantation of artificial hair made of polyethylene terephthalate and implantation of artificial hair made of polybutylene terephthalate shows that artificial hair made of PET is too hard and tends to shrink during implantation and easily curls or stands up when the wearer is sleeping. On the contrary, artificial hair made of PBT is flexible like willow, so that it is hard to break or deform due to bending, and scarcely shrinks.

Antibacterial Ability Test of Artificial Hair

FIG. 4 is a table showing the results of tests on the antibacterial ability of artificial hair. Two monofilaments each of: artificial hair made of polybutylene terephthalate with addition of 1.0% silver zeolite (sample A); artificial hair made of polybutylene terephthalate with addition of 1.5% silver zeolite (sample B); and artificial hair made of polybutylene terephthalate without addition of silver zeolite (sample C) were used as samples to carry out the antibacterial ability tests. These samples were inoculated with Staphylococcus aureus, and the number of viable fungi immediately after the inoculation was compared to the number of viable fungi after 18 hours had elapsed.

As shown in FIG. 4, while artificial hair made of polybutylene terephthalate containing 1.0% silver zeolite is recognized to have antibacterial effect, artificial hair made of polybutylene terephthalate containing 1.5% silver zeolite has a much higher antibacterial effect.

As described above, artificial hair according to the present invention has the following properties:

(1) Excellent characteristics in both safety and fatigue strength against bending compared to artificial hair made of polyethylene terephthalate fiber can be attained since polybutylene terephthalate used as the principal component of the artificial hair according to the present invention is subjected to melt spinning without using any organic solvent;

(2) The stiffness of polybutylene terephthalate fiber can be improved and artificial hair having excellent flexibility and suitable elasticity can be attained so as to permit a fluffy hairstyle since the artificial hair according to the present invention contains the powder of silver ceramics.

(3) The stiffness of the polybutylene terephthalate fiber can be improved, and artificial hair having excellent flexibility and suitable elasticity can be achieved so as to permit a fluffy hairstyle since the artificial hair according to the present invention contains the powder of silver ceramics. In addition, due to the silver ceramics content, artificial hair according to the present invention has high antibacterial activity that can prevent the invasion of bacteria from a wound formed incident to the implantation operation and prevent the implanted artificial hair from falling off due to suppuration. As a consequence, the fixation rate of implanted artificial hair can be improved.

(4) The antibacterial effect can be further improved since the artificial hair of the present invention is subjected to a mechanical delustering treatment for treating the surface of the monofilaments of polybutylene terephthalate fiber containing the powder of silver ceramics, and the surfaces of the powder of silver ceramics existing at the surfaces of the monofilaments are exposed due to this treatment.

The above described examples are not intended to limit the scope of the present invention, as one skilled in the art can, in view of the present disclosure, expand such examples to correspond with the subject matter of the invention claimed below. For example, powdered additives other than the preferred silver ceramic can be used, especially, other anti-bacterial ceramics such as silver zeolite, silver apatite, silver phosphoric acid calcium, silver phosphoric acid zirconium and so on, which increase the stiffness of the PBT and which can be tolerated by the human body without toxicity.

What is claimed is:

1. Artificial hair for implantation comprising monofilaments of a fiber having a principal component of polybutylene terephthalate, wherein said monofilaments contain powder of silver ceramics.

2. Artificial hair for implantation according to claim 1, wherein said powder has a particle size of 5.0 $\mu$m or less.

3. Artificial hair for implantation according to claim 2, wherein said powder of the silver ceramics is present in said monofilaments in a concentration of 0.3% to 3.0%, by weight.

4. Artificial hair for implantation according to claim 3, wherein said silver ceramics are at least one of silver zeolite, silver apatite, silver phosphoric acid calcium, and silver phosphoric acid zirconium.

5. Artificial hair for implantation according to claim 4, wherein said monofilaments have a surface texture resulting from a delustering treatment.

6. Artificial hair for implantation according to claim 2, wherein said silver ceramics are at least one of silver zeolite, silver apatite, silver phosphoric acid calcium and silver phosphoric acid zirconium.

7. Artificial hair for implantation according to claim 6, wherein said monofilaments have a surface texture resulting from a delustering treatment.

8. Artificial hair for implantation according to claim 1, wherein said powder of silver ceramics is present in said monofilaments in a concentration of 0.3% to 3.0%, by weight.

9. Artificial hair for implantation according to claim 1, wherein said silver ceramics are at least one of silver zeolite, silver apatite, silver phosphoric acid calcium and silver phosphoric acid zirconium.

10. Artificial hair for implantation according to claim 9, wherein said monofilaments have a surface texture resulting from a delustering treatment.

11. Artificial hair for implantation according to claim 1, wherein the polybutylene terephthalate has a number average molecular weight of 10,000 to 60,000.

12. Artificial hair for implantation according to claim 11, wherein the polybutylene terephthalate has a number average molecular weight of 20,000 to 40,000.

13. Artificial hair for implantation according to claim 1, wherein the monofilaments have a diameter within a range of 80 $\mu$m to 110 $\mu$m.

14. Artificial hair for implantation according to claim 13, wherein the monofilaments have a diameter within a range of 90 $\mu$m to 110 $\mu$m.

15. A process for producing artificial hair for implantation, said process comprising:

mixing particles of silver ceramics into a masterbatch comprising a principal component of polybutylene terephthalate, wherein the silver ceramics have a particle size of is 5.0 $\mu$m or less and are present in the mixture in a concentration of 0.3% to 3.0%, by weight; and subsequently melt spinning the mixture to form monofilaments.

16. The process for producing artificial hair for implantation according to claim 15, wherein the silver ceramics are at least one of silver zeolite, silver apatite, silver phosphoric acid calcium and silver phosphoric acid zirconium.

17. The process for producing artificial hair for implantation according to claim 16, further comprising subjecting the monofilaments to a delustering treatment.

18. The process for producing artificial hair for implantation according to claim 15, further comprising subjecting the monofilaments to a delustering treatment.

* * * * *